(12) United States Patent
Cheng et al.

(10) Patent No.: US 12,043,861 B2
(45) Date of Patent: Jul. 23, 2024

(54) MALARIA DETECTION METHOD AND DEVICE

(71) Applicants: Yu-Chung Norman Cheng, Northville, MI (US); Mitchelle V. Zolotarevsky, W. Bloomfield, MI (US)

(72) Inventors: Yu-Chung Norman Cheng, Northville, MI (US); Mitchelle V. Zolotarevsky, W. Bloomfield, MI (US)

(73) Assignee: Yu-Chung Norman Cheng, Northville, MI (US)

( * ) Notice: Subject to any disclaimer, the term of this patent is extended or adjusted under 35 U.S.C. 154(b) by 566 days.

(21) Appl. No.: 16/808,807

(22) Filed: Mar. 4, 2020

(65) Prior Publication Data

US 2021/0277439 A1   Sep. 9, 2021

(51) Int. Cl.
| | |
|---|---|
| *C12Q 1/04* | (2006.01) |
| *G01N 27/06* | (2006.01) |
| *G01N 27/22* | (2006.01) |
| *G01N 33/49* | (2006.01) |

(52) U.S. Cl.
CPC .............. *C12Q 1/04* (2013.01); *G01N 27/06* (2013.01); *G01N 27/221* (2013.01); *G01N 33/49* (2013.01); *G01N 2333/445* (2013.01); *G01N 2469/00* (2013.01)

(58) Field of Classification Search
CPC ........... G01N 27/221; G01N 2333/445; G01N 27/06; G01N 33/49; C12Q 1/04
See application file for complete search history.

(56) References Cited

U.S. PATENT DOCUMENTS

| | | | |
|---|---|---|---|
| 6,255,954 | B1 | 7/2001 | Brown et al. |
| 9,575,052 | B2 | 2/2017 | Grimberg et al. |
| 2018/0128823 | A1* | 5/2018 | Lee ................... B01L 3/502753 |
| 2018/0259488 | A1 | 9/2018 | Sierra et al. |

FOREIGN PATENT DOCUMENTS

| | | |
|---|---|---|
| CN | 1839313 A | 9/2006 |
| JP | 2002365257 A | 12/2002 |
| WO | 2017/066347 A1 | 4/2017 |
| WO | 2019/016691 A1 | 1/2019 |

OTHER PUBLICATIONS

Luka et al. Label-Free Capacitive Biosensor for Detection of Cryptosporidium; Sensors, vol. 19, No. 258, pp. 1-9. (Year: 2019).*
Shirzadfar et al. Optimize the Geometrical Parameters of Interdigital Micro-Electrodes Used in Bioimpedance Sensing System; Journal of Nano- and Electronic Physics, vol. 10, No. 5, pp. 1-4. (Year: 2018).*
Soraya et al. Ultrasensitive and Label-Free Biosensor for the Detection of Plasmodium Falciparum Histidine Rich Protein II in Saliva; Scientific Reports, vol. 9, pp. 1-10. (Year: 2019).*
Zhang et al. Dep-on-a-Chip: Dielectrophoresis Applied to Microfluidic Platforms; Micromachines, vol. 10, No. 423, pp. 1-22. (Year: 2019).*
Kumar et al. Label-Free Electrochemical Detection of Malaria-Infected Red Blood Cells; RSC Advances, vol. 6, pp. 75862-75869. (Year: 2016).*
Honrado et al. Dielectric Characterization of Plasmodium Fzlciparum-Infected Red Blood Cells Using Microfluidic Impedance Cytometry; Journal of the Royal Society Interface, vol. 15, pp. 1-11. (Year: 2018).*
Anonymous. Lactate Plus Instructions for Use Manual; pp. 1-65. downloaded from: http://www.laktate.com/wp-content/uploads/2013/10/User%20Manual_Lactate%20Plus_EN.pdf on Feb. 10, 2023. (Year: 2019).*
Sharokhian et al. Voltammetric Behavior and Determination of Trace Amounts of Omeprazole Using an Edge-Plane Pyrolytic Graphite Electrode; Iranian Journal of Pharmaceutical Research, vol. 14, No. 2, pp. 465-471. ( Year: 2015).*
Anonymous. ASTI Summary of Final Conductivity Sensor Cleaning Procedures; pp. 1-3. downloaded from: https://www.astisensor.com/Conductivity_Sensor_Final_Cleaning_Procedure.pdf on Feb. 13, 2023. (Year: 2016).*
Anonymous. Technotes Chlorine Added to Alconox for Medical Cleaning; pp. 1. downloaded from: https://technotes.alconox.com/detergents/alconox/chlorine-added-alconox-medical-cleaning/# on Feb. 13, 2023. (Year: 2014).*
Ono, M. Everything You Wanted to Know About Bleach but Were Afraid To Ask; News and Views, vol. 6, No. 5, pp. 1. downloaded from: https://www.scripps.edu/newsandviews/e_20060213/bleach.html on Feb. 13, 2023. (Year: 2006).*
Anonymous. Chlorine Bleach Disinfecting and Sanitizing Chart Companion Document; Washington State Department of Health, pp. 1-2. downloaded from: https://files4.1.revize.com/adamscounty/document_center/Health/Bleach%20Disinfecting%20Chart.pdf on Feb. 13, 2023. (Year: 2014).*
Shuster et al. Utility of Resistance and Capacitance Response in Sensors Based on Monolayer-Capped Metal Nanoparticles; The Journal of Physical Chemistry Letters, vol. 2, pp. 1912-1916. (Year: 2011).*
Giacometti et al. Electrical and Magnetic Properties of Hemozoin Crystals; Applied Physics Letters; vol. 113, pp. 1-5. (Year: 2018).*
Giacometti et al. TMEK: A Quantitative Rapid Diagnostic Test for Malaria; Transactions of the Royal Society of Tropical Medicine and Hygiene, vol. 113, pp. S70-71. (Year: 2019).*

(Continued)

*Primary Examiner* — Jeanette M Lieb
*Assistant Examiner* — Paul C Martin
(74) *Attorney, Agent, or Firm* — The Dobrusin Law Firm, P.C.

(57) ABSTRACT

An method of malaria detection includes providing an interdigitated sensor having a first electrode with a plurality of fingers and a second electrode with a plurality of fingers, interspersed and spaced apart from the fingers of the first electrode. A quantity of blood to be tested is received on the sensor. The blood is to be dried and is measured for at least one measurable characteristic, including a resistance of the blood. The presence of malaria infected blood is determined based on a comparison between the measurable characteristics and a predetermined threshold related to the measurable characteristics.

16 Claims, 5 Drawing Sheets

(56) References Cited

OTHER PUBLICATIONS

Milesi et al. TMEK: A Lab-on-Chip Diagnostic Test for the Malaria Disease; II Nuovo Cimento, vol. 18, pp. 1-8. (Year: 2021).*

P. Gascoyne, J. Satayavivad, and M. Ruchirawat, Microfluidic approaches to malaria detection, Acta Trop., 89: 357-369, 2004.

P. Gascoyne, R. Pethig, J. Satayavivad, F. F. Becker, and M. Ruchirawat, Dielectrophoretic detection of changes in erythrocyte membranes following malarial infection, Biochim. Biophys. Acta, 1323(2): 240-252, 1997.

P. Gascoyne, C. Mahidol, M. Ruchirawat, J. Satayavivad, P. Watcharasit, and F. Becker, Microsample preparation by dielectrophoresis: isolation of malaria, Lab. Chip 2(2): 70-75, 2002.

E. Du, S. Ha, M. Diez-Silva, M. Dao, S. Suresh, and A. P. Chandrakasan, Electric impedance microflow cytometry for characterization of cell disease states, Lab Chip, 13: 3903-3909, 2013.

D. M. Newman, J. Heptinstall, R. J. Matelon, L. Savage, M. L. Wears, J. Beddow, M. Cox, H. D. F. H. Shallig, and P. F. Mens, A magneto-optic route toward the in vivo diagnosis of malaria: preliminary results and preclinical trial data, Biophys. J., 95: 994-1000, 2008.

Benevento G, "Development of an impedance-based diagnostic instrument for malaria", Masters Thesis, Politecnico di Milano, 2018 [retrieved from internet Jul. 12, 2022].

Sivaraj L. et al., "Portable biosensor for chronic malaria detection", 17th International Symposium on Quality Electronic Design (ISQED), 2016, pp. 248-251, doi: 10.1109/ISQED.2016.7479208.

Du E et al., "Electric impedance microflow cytometry for characterization of cell disease states", HHS Author Manuscripts, 2014, PMC3830000 [url: https://www.ncbi.nlm.nih.gov/pmc/articles/PMC3830000/] published in final form as, Lab on a Chip, 2013, 13(19):3903-3909. doi: 10.1039/c3lc50540e.

Australia First Examination Report dated Jul. 28, 2022, Application No. 2020202761.

* cited by examiner

MALARIA DETECTION METHOD AND DEVICE

FIELD OF INVENTION

The present invention relates to the field of malaria detection and specifically to a method and device for detecting the presence of malaria within a blood sample using electrical properties.

BACKGROUND

Malaria remains one of the most common diseases in the world, with approximately 200 million cases of malaria infection estimated to occur each year. Approximately 600,000 patients die annually from malaria, including many children under the age of 10. While treatments for malaria have been developed, there is still a need for further development in the inexpensive detection and rapid diagnosis of malaria to be used in regions lacking of resources.

Current methods for detecting malaria are focused largely on analysis of patient's blood. To do this, blood must be drawn from the patient, treated, and commonly examined under a microscope to determine the presence of infected red blood cells. However, different detection methods have various drawbacks. First, preparation and analysis of individual treated blood samples under a microscope takes considerable time. Often times, patients are located in remote areas and waiting for the examine significantly interrupts patients' daily life. When methods other than a microscope are used to detect malaria within blood, the necessary scientific equipment associated with those methods is not easily portable or requires electricity, and thus those methods cannot be deployed effectively. Moreover, the cost of these methods may be considerable as well, specifically when each blood sample must be treated and examined.

Accordingly, an improved method and device for detection of malaria is needed.

SUMMARY

A method of detecting malaria from a blood sample is generally presented. The method comprises providing an interdigitated sensor having a first electrode with a plurality of fingers and a second electrode with a plurality of fingers. The fingers of the first electrode are interspersed with the fingers of the second electrode and there is a space between the interspersed fingers. The method further comprises receiving a quantity of blood and applying the quantity of blood to the interdigitated sensor. The method further comprises measuring the quantity of blood for at least one measurable characteristic, wherein the at least one measurable characteristic includes a resistance of the blood. The method further comprises determining the presence of malaria infected blood based on a comparison between the at least one measurable characteristic and a predetermined threshold related to the at least one measurable characteristic.

In an embodiment, the at least one measurable characteristic further includes a capacitance of the blood. The predetermined threshold includes a threshold based on both the resistance and capacitance of the blood.

In an embodiment, the method may further comprise confirming a determination of the presence of malaria infected red blood cells by performing a confirmation test on a second blood sample from the same source as the first blood sample.

In an embodiment, the space in between the fingers may be 1 micrometer. The quantity of blood applied to the sensor may be 0.5 microliter. The process of applying the blood to the sensor may comprise applying the quantity of blood adjacent to the sensor or along an edge of the sensor and swiping the quantity of blood perpendicularly across interspersed fingers only once to disperse the blood over the sensor.

In an embodiment, a device for determining the presence of malaria in a blood sample is provided. The device may be a handheld device that includes a body, a user interface including a graphic interface, and an interdigitated sensor connected to the handheld body. The interdigitated sensor may include a first electrode having a plurality of fingers and a second electrode having a plurality of fingers. The first electrode fingers may be interspersed with the second electrode fingers and a space may be provided between the fingers. The interdigitated sensor may be configured to receive a quantity of blood applied thereon and to measure the quantity of blood for at least one measurable characteristic, such as a resistance of the blood. The handheld device may be used to determine the presence of malaria in the quantity of blood based on a comparison between the at least one measurable characteristic and a predetermined threshold related to the at least one measurable characteristic.

In an embodiment, a method of cleaning a sensor is provided. The method includes the steps of: creating a cleaning solution, wherein the cleaning solution comprises water and bleach: placing the sensor in the cleaning solution and putting the cleaning solution and sensor into an ultrasound cleaning device: removing the sensor from the cleaning solution and rinsing the sensor; testing the sensor in air for a predetermined resistance threshold; and testing the sensor in air for a predetermined capacitance threshold. The cleaning solution may be 20% concentrated bleach and 80% water. In an embodiment the predetermined resistance threshold may be 100 M ohms and the predetermined capacitance threshold may be 40.0±1.0 pf/m per pair of fingers and per its length.

BRIEF DESCRIPTION OF THE DRAWINGS

The operation of the invention may be better understood by reference to the detailed description taken in connection with the following illustrations, wherein.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 4:
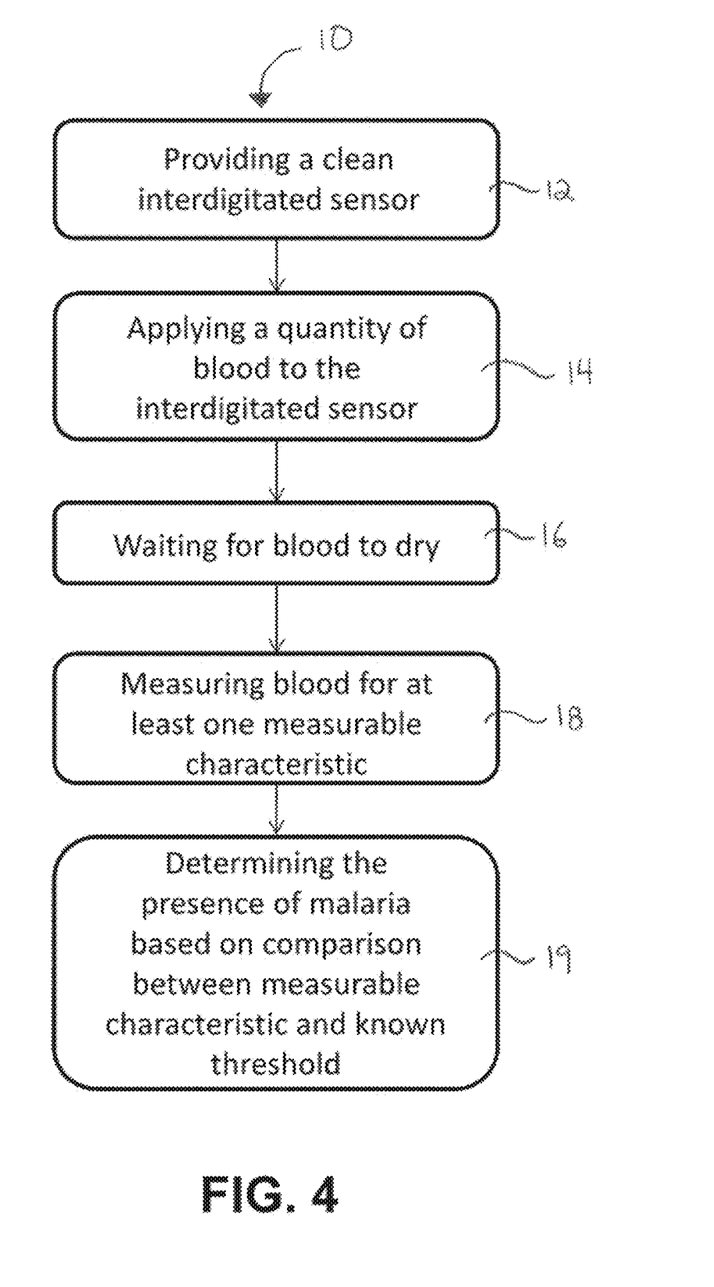
FIG. 4 illustrates a flow chart for a method of determining the presence of malaria in blood.

A method 10 of detecting malaria in blood 32, and related device 50 for malaria detection, are generally presented. The method 10 and device 50 are generally configured to sustain blood within a sensor and measure various attributes, such as the resistance and capacitance of the blood to determine the presence of malaria within the blood.

Figure 1:
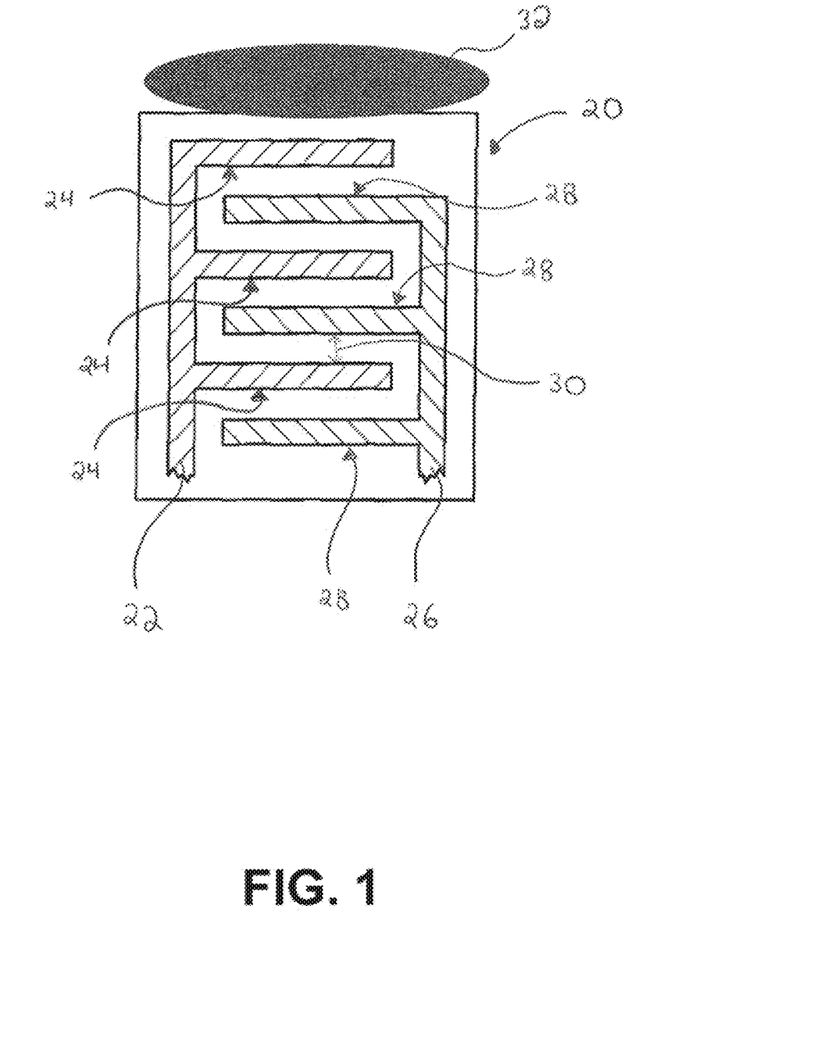
FIG. 1 illustrates an interdigitated sensor for use in measuring the resistance and capacitance of blood.

In a first step 12, an interdigitated sensor 20 is provided. The interdigitated sensor 20 may comprise a first electrode 22 having a plurality of fingers 24 and a second electrode 26 having a plurality of fingers 28, as best illustrated in FIG. 1. The interdigitated sensor 20 may be printed on a quartz wafer or may be disposed on any similar medium with a laser printing technology. The first and second electrodes 22, 26 may be interspersed such that the fingers 24 of the first electrode 22 are disposed between the fingers 28 of the second electrode 26 and vice versa. The electrodes 22, 26 may include any appropriate number of fingers 24, 28, such as three fingers as shown in FIG. 1, and the fingers 24, 28 may be any appropriate size, such as approximately 0.9 millimeter in length and approximately 1 micrometer in width.

The electrodes 22, 26 may be arranged to provide a space 30 between the respective fingers 24, 28. The space 30 may be defined as the gap between adjacent fingers 22, 26. In an embodiment, the space 30 between the fingers 24, 28 may be generally constant throughout the entire sensor, as illustrated in FIG. 1. However, in some embodiments it may be contemplated that the spacing of the fingers 24, 28 may vary.

The fingers 24, 28 may be arranged and spaced apart such that the space 30 between them is less than one or more dimensions of a standard red blood cell. For example, a standard red blood cell has a diameter of approximately 6-8 microns. The space 30 between the fingers 24, 28 may be set at a distance less than the diameter or less than another dimension of the red blood cell, such as a space 30 of 1 micron, to allow the red blood cells to span the space 30 while maintaining contact with both electrodes 22, 26. This arrangement allows the electrodes 24, 28 to then measure traits of the dried blood, such as resistance and capacitance.

In a second step 14, a quantity of blood 32 may be drawn and applied to the interdigitated sensor 20. The blood 32 may be drawn from a patient to be tested for the presence of malaria. Based on the size of the interdigitated sensor 20, the blood sample will not need to be substantial. In an embodiment, a 0.5 microliter sample may be used.

The blood sample 32 may be applied along an edge of the sensor, such as shown in FIG. 1. The blood 32 may then be applied to the sensor 20 by swiping the blood 32 perpendicularly across fingers 24, 28 over the entire sensor 20, in order to evenly disperse the blood 32 and remove its excessive plasma above the fingers 24, 28.

Figure 2A:
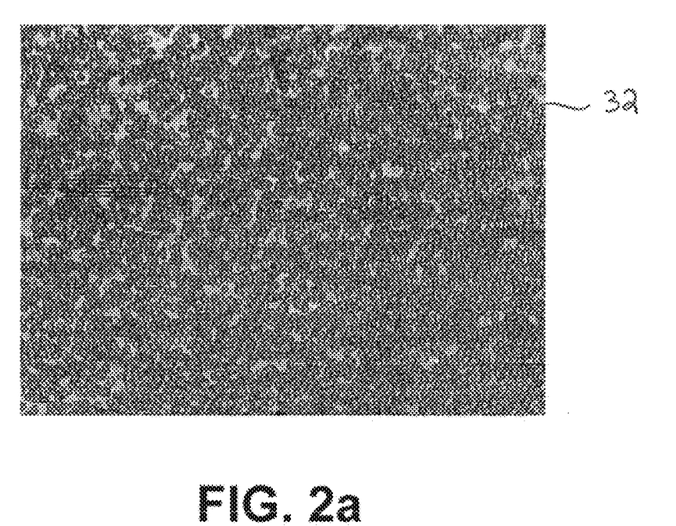
FIG. 2a illustrates a blood sample on an interdigitated sensor that has been smeared once.
Figure 2B:
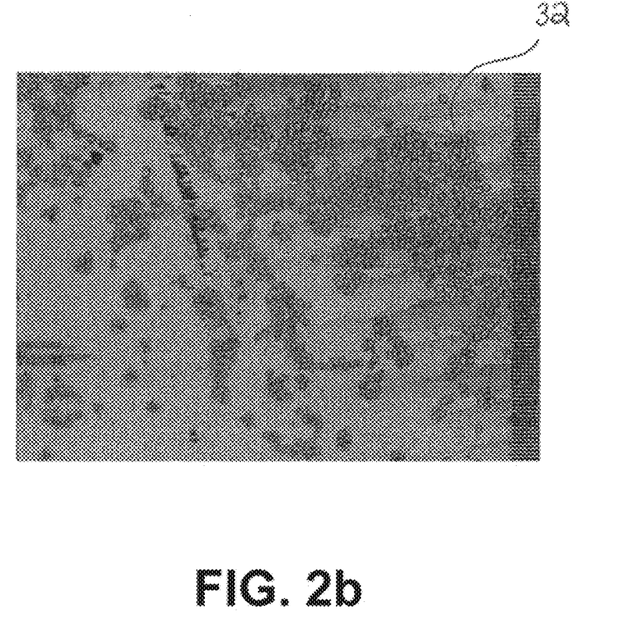
FIG. 2b illustrates a blood sample on an interdigitated sensor that has been smeared twice.

In an embodiment, the blood 32 is swiped only once over the entire sensor to prevent losing red blood cells for an accurate measurement. As illustrated in FIGS. 2a and 2b, any swiping of the blood 32 beyond a singly swipe may lead to loss of red blood cells and compromise any measurements taken. Specifically, FIG. 2a illustrates a single swipe blood sample 32 that includes a higher density of red blood cells and FIG. 2b illustrates a double swipe blood sample that has a lower density of red blood cells than the single swipe sample.

In a third step 16, the blood 32 applied to the sensor 20 should be allowed to completely dry. While the drying time may vary, in an embodiment blood 32 may be given five (5) minutes to completely dry on the sensor before any measurements are taken on the blood.

In a fourth step 18, the blood 32 may be measured for one or more measurable characteristics. The measureable characteristics may include the resistance of the blood 32, the capacitance of the blood 32, or any other measurable characteristic. The resistance may specifically be measured by applying a small current to the first electrode 22 and measuring the voltage across the first and second electrodes 22, 26. In addition, the capacitance of the blood 32 may be measured by applying a known current, charging and discharging the blood 32, measuring the rate of rise of the resulting voltage between the electrodes 22, 26, and then calculating the capacitance.

Figure 3:
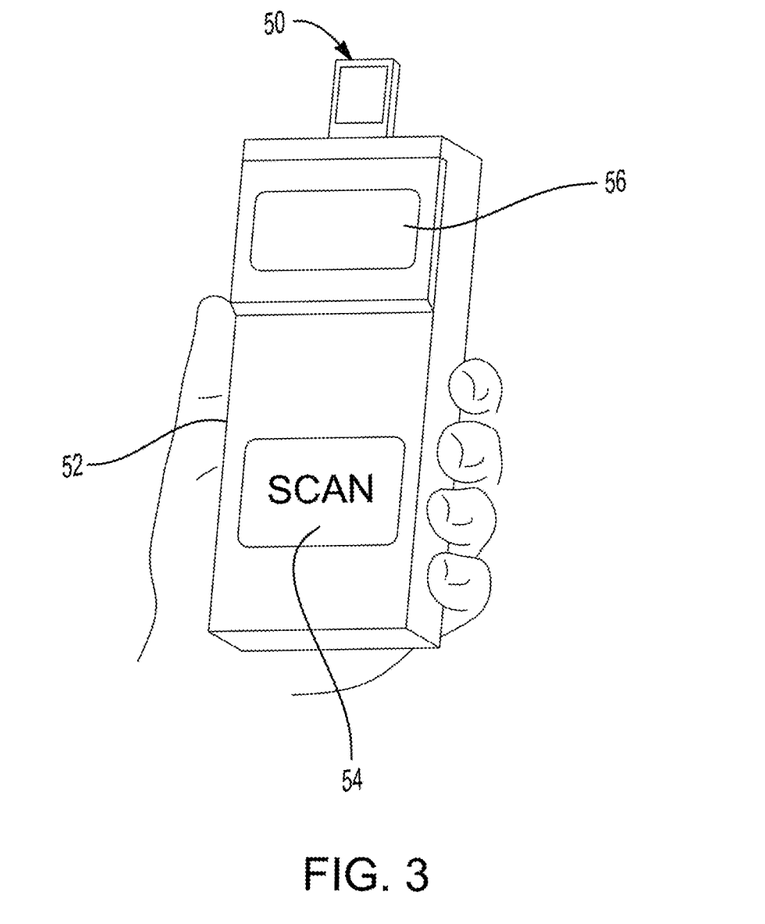
FIG. 3 illustrates a handheld device for determining the presence of malaria in blood.

To perform the measurement tasks, the first and second electrodes 22, 26 of the interdigitated sensor 20 may be connected to and fully integrated with a measuring device, such as a handheld measuring device 50 as illustrated in FIG. 3. The handheld measuring device 50 may be capable of measuring any number of other measurable characteristics, including inductance, gain, frequency, and other measurable characteristics. The handheld measuring device 50 may include a user interface 52, including inputs 54 such as a scan input to direct the device 50 to initiate measurement of the blood, or a function selection input to select measurement functions. The device 50 may further include a graphic interface or display 56 to display test results or other information related to measurement and testing of the blood 32.

In a fifth step 19, the measured characteristics of the blood 32 may be compared with known thresholds of the measured characteristics to determine whether a blood sample contains malaria infected red blood cells. Malaria infected red blood cells enclose malaria parasites, which produce hemozoin biocrystals inside the body of each parasite. The hemozoin crystals increase the electrical conductivity of the red blood cell, thus lowering the resistance of malaria infected blood. Based on testing of malaria infected and non-infected blood, resistance alone or in combination with capacitance thresholds may be determined for deciphering between blood that is infected with malaria and blood that is not infected with malaria.

In an embodiment, blood samples that are below a given threshold, such as a resistance threshold, may be deemed "high risk" or "high probability" blood meaning that there is a high probability that the blood 32 contains malaria infected red blood cells. Further testing can then be conducted on high risk blood samples to confirm the presence of malaria within the blood 32. For example, a second blood sample may be drawn from the same source as the first blood sample 32 and tested the methods described herein or using other conventional methods to confirm a determination of the presence of malaria, or to confirm malaria in a high probability outcome.

In an embodiment, a measurable characteristic, such as resistance, may be used in conjunction with other measurable characteristics, such as capacitance or other characteristics, to determine whether a blood sample 32 is infected or non-infected. The determination process may include using a lookup table, either manually or digitally within the handheld reader or on an additional computing device, to determine a threshold based on two or more measurable characteristics.

Figure 5:
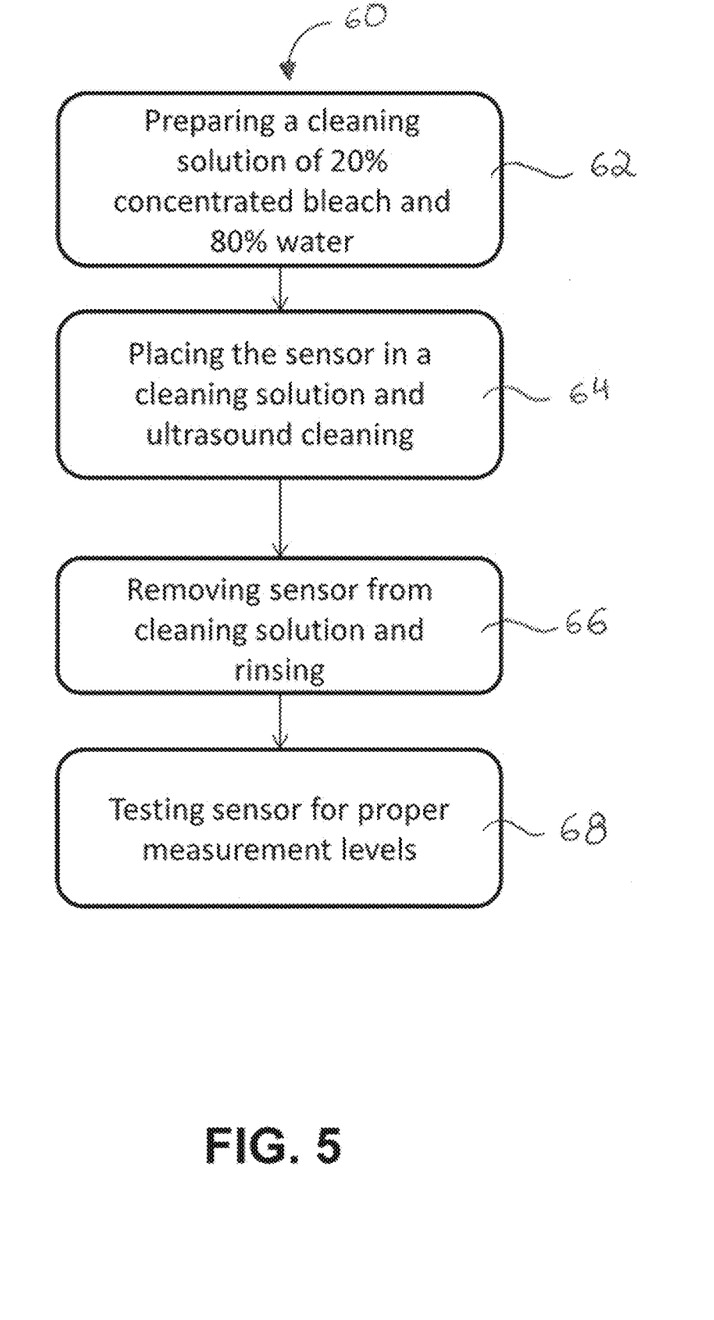
FIG. 5 illustrates a flow chart for a method of cleaning a sensor.

After use, the sensor 20 may require cleaning to allow for reuse. It will be appreciated that proper cleaning is vital in order to avoid false positive results or any skewed or altered results. In an embodiment, a method 60 of cleaning the sensor 20 comprises a step of creating a cleaning solution 62. The cleaning solution may be a 20% concentrated bleach solution (such as prepared from the concentrated bleach with 8.25% of sodium hypochlorite) that comprises 20% bleach and 80% water. In a second step 64, the sensor 20 may be placed in a beaker filled with the cleaning solution and placed within an ultrasound cleaner for a period of time. The ultrasound cleaning may last for any appropriate amount of time to adequately clean the sensor, such as a period of 10 minutes. After the ultrasound cleaning is complete, in a third step 66, the sensor 20 may be removed from the beaker and rinsed with water to remove any bleach or cleaning solution. To test for adequate cleaning, in a fourth step 68, the resistance and capacitance of the sensor 20 may then be tested to measure if predetermined resistance and capacitance levels that match an open circuit in air are met. In an embodiment, the desired predetermined resistance threshold of a clean sensor in the air may be infinite, or at least 100 MQ, and predetermined capacitance threshold of a clean sensor with a substrate of quartz or silicon dioxide in the air may be approximately 40 pf±1.0 pf/m per pair of fingers and per its length.

It will be appreciated that proper cleaning of the sensor may be vital to the sensor's reuse and total life. Because the space 30 between electrodes 22, 26 on each sensor is very small, any conductive debris left on the sensor 20 can create a short circuit or lead to a low resistance value during a measurement. In addition to cleaning sensors 20 after use, it is also important to use the cleaning process before the first use to remove any debris that may be present from the manufacturing process. While some manufacturers may recommend other processes for cleaning new sensors 20, such as gently rubbing the sensor 20 with methanol, the cleaning process described herein is proven to be more effective without yielding to the sensor 20.

It will be further appreciated that other cleaning methods, such as uses of other cleaning solutions, cleaning methods, durations, or other derivations from the described method, may fail to adequately clean the sensor 20 or may result in degrading or damaging the sensor 20 or reducing the sensor's life.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

Having thus described the invention, we claim:

1. A method of detecting malaria within a blood sample, the method comprising:
   providing an interdigitated sensor, the interdigitated sensor comprising:
      a first electrode having a plurality of fingers;
      a second electrode having a plurality of fingers;
      wherein the plurality of fingers of the first electrode are interspersed with the plurality of fingers of the second electrode and have a space therebetween:
   receiving a quantity of blood;
   applying the quantity of blood adjacent to the interdigitated sensor or along an edge of the interdigitated sensor and swiping the quantity of blood perpendicularly across the plurality of fingers of the first and second electrodes only once to disperse the quality of blood over the interdigitated sensor;
   allowing the quantity of blood to dry on the interdigitated sensor;
   measuring the quantity of blood, including non-infected red blood cells, for at least one measurable characteristic, wherein the at least one measurable characteristic includes a resistance of the quantity of blood, which detects the presence of hemozoin crystals inside red blood cells; and
   determining the presence of malaria infected blood based on a comparison between the at least one measurable characteristic and a predetermined threshold related to the at least one measurable characteristic;
   wherein the space in between the plurality of fingers is 6 microns or less, which corresponds to a dimension of the red blood cells, such that the red blood cells span the space while maintaining contact with the plurality of fingers from both of the first and second electrodes.

2. The method of claim 1, wherein the at least one measurable characteristic further includes a capacitance of the quantity of blood, which detects the presence of malaria parasites inside the red blood cells.

3. The method of claim 2, wherein the predetermined threshold includes a threshold based on both the resistance and the capacitance of the quantity of blood.

4. The method of claim 1, further comprising cleaning the interdigitated sensor and subsequently checking conditions of the cleaned interdigitated sensor through resistance and capacitance measurements of the interdigitated sensor, before testing another quantity of blood.

5. The method of claim 4, further comprising the steps of:
   creating a cleaning solution, wherein the cleaning solution comprises water and bleach;
   placing the interdigitated sensor within the cleaning solution;
   placing the interdigitated sensor in the cleaning solution within an ultrasound cleaning device;
   removing the interdigitated sensor from the cleaning solution and rinsing the interdigitated sensor;
   testing the interdigitated sensor in air for a predetermined resistance threshold; and
   testing the interdigitated sensor in air for a predetermined capacitance threshold.

6. The method of claim 5, wherein the predetermined resistance threshold is 100 M ohms; and wherein the capacitance threshold is 40.0±1.0 pf/m per pair of the plurality of fingers and per a length of the plurality of fingers.

7. The method of claim 6, wherein the interdigitated sensor has a substrate of quartz or silicon dioxide.

8. The method of claim 5, wherein the cleaning solution comprises 80% water and 20% concentrated bleach; and wherein the bleach is concentrated bleach with 8.25% of sodium hypochlorite.

9. The method of claim 8, wherein the interdigitated sensor in the cleaning solution is placed within the ultrasound cleaning device for at least 10 minutes.

10. The method of claim 1, wherein the space in between the plurality of fingers is 1 micrometer.

11. The method of claim 10, wherein the quantity of blood comprises as little as 0.5 microliter of blood.

12. The method of claim 5, wherein the plurality of fingers have a length of 0.9 millimeter.

13. The method of claim 12, wherein the plurality of fingers have a width of 1 micrometer.

14. The method of claim 1, wherein the quantity of blood is allowed to dry on the interdigitated sensor for no more than five minutes.

15. The method of claim 1, wherein the plurality of fingers of the first electrode are a plurality of straight fingers arranged in parallel to one another; wherein the plurality of fingers of the second electrode are a plurality of straight fingers arranged in parallel to one another; and wherein the plurality of fingers respectively of the first and second electrodes include at least 3 fingers.

16. A method of detecting malaria within a blood sample, the method comprising:
   providing an interdigitated sensor, the interdigitated sensor comprising:
      a first electrode having a plurality of straight fingers arranged in parallel;
      a second electrode having a plurality of straight fingers arranged in parallel;
      wherein the plurality of straight fingers of the first electrode are interspersed with the plurality of straight fingers of the second electrode and have a space therebetween;
   receiving a quantity of blood;
   applying the quantity of blood adjacent to the interdigitated sensor or along an edge of the interdigitated sensor and swiping the quantity of blood perpendicularly across the plurality of straight fingers of the first and second electrodes only once to disperse the quantity of blood over the interdigitated sensor;
   allowing the quantity of blood to dry on the interdigitated sensor;
   measuring the quantity of blood, including non-infected red blood cells, for at least one measurable characteristic, wherein the at least one measurable characteristic includes a resistance of the quantity of blood, which detects the presence of hemozoin crystals inside red blood cells; and
   determining the presence of the hemozoin crystals inside the red blood cells based on a comparison between the at least one measurable characteristic and a predetermined threshold related to the at least one measurable characteristic;
   wherein the space in between the plurality of straight fingers is 6 microns or less, which corresponds to a dimension of the red blood cells, such that the red blood cells span the space while maintaining contact with the plurality of straight fingers from both of the first and second electrodes;
   wherein the plurality of straight fingers have a length of 0.9 millimeter and a width of 1 micrometer.

* * * * *